United States Patent [19]

Wegman

[11] 4,429,165
[45] Jan. 31, 1984

[54] HYDROFORMYLATION PROCESS

[75] Inventor: Richard W. Wegman, Cross Lanes, W. Va.

[73] Assignee: Union Carbide Corporation, Danbury, Conn.

[21] Appl. No.: 391,679

[22] Filed: Jun. 24, 1982

[51] Int. Cl.³ .............................................. C07C 45/49
[52] U.S. Cl. ................................... 568/487; 568/462; 568/909
[58] Field of Search ........................ 568/487, 462, 909

[56] References Cited

U.S. PATENT DOCUMENTS

| | | | |
|---|---|---|---|
| 3,356,734 | 12/1967 | Kuraishi et al. | 568/487 |
| 4,151,208 | 4/1979 | Pretzer et al. | 568/487 |
| 4,201,868 | 5/1980 | Slinkard | 568/487 |
| 4,225,517 | 9/1980 | Gane | 568/487 |
| 4,260,154 | 4/1981 | Gane et al. | 568/487 |
| 4,320,230 | 3/1982 | Doyle | 568/487 |
| 4,361,706 | 11/1982 | Habib | 568/487 |

FOREIGN PATENT DOCUMENTS

| | | | |
|---|---|---|---|
| 52-133914 | 11/1977 | Japan | 568/487 X |
| 52-136110 | 11/1977 | Japan | 568/487 X |
| 52-136111 | 11/1977 | Japan | 568/487 X |

OTHER PUBLICATIONS

Wayne Pretzer and Thaddeus Kobylinski, Annals New York Academy of Sciences, 333, 58, (1980).

*Primary Examiner*—Werren B. Lone
*Attorney, Agent, or Firm*—Francis M. Fazio

[57] ABSTRACT

Process for selective production of acetaldehyde and dimethyl acetal by the reaction of methanol with carbon monoxide in contact with a catalyst containing cobalt atom, halide atom and a mixture of a trivalent phosphorus compound and a trivalent nitrogen compound. The amount of trivalent nitrogen compound in its mixture varies from 5 mole percent to 50 mole percent of such mixture.

29 Claims, No Drawings

HYDROFORMYLATION PROCESS

BACKGROUND OF THE INVENTION

The production of organic compounds from synthesis gas has been carried out for a significant period of time. It is well known that one can produce methanol from synthesis gas and that methanol can be further reacted by hydroformylation, homologation and carbonylation reactions to produce acetaldehyde, ethanol and acetic acid, respectively. The difficulties, however, have resided in the ability to carry out one of these chosen reactions to selectively produce the desired compound at an acceptable conversion rate.

In the case of methanol hydroformylation the reaction is generally preferably catalyzed using a mixture of a cobalt compound and a halogen as the promoter, though many other metal compounds and promoters have been tried. In addition, the prior art has disclosed the use of secondary activators in conjunction with the metal catalysts and promoters. These secondary activators can be other metallic salts or compounds, amines, phosphorus compounds and a multitude of other compounds that have been disclosed in the published literature. Thus, a typical catalyst system contains the metal catalyst, the promoter and the secondary activator. Though a significant amount of literature does exist, to our knowledge it does not disclose or suggest our improved invention.

In U.S. Pat. No. 3,356,734, issued to Kuraiski et al. on Dec. 5, 1967, there is disclosed the process for producing acetaldehyde using a cobalt catalyst promoted by a halogen promoter. It makes no reference to trivalent nitrogen or trivalent phosphorus compounds.

U.S. Pat. No. 4,151,208, issued to Pretzer et al. on Apr. 24, 1979, claims the use of cobalt (II) tetraaromaticporphine compounds as catalysts and an iodine promoter to improve selectivity. The only selectivity value reported was about 62 mole percent.

The use of a halide-free catalyst is disclosed in U.S. Pat. No. 4,201,868, issued to Slinkard on May 6, 1980. The halide-free catalysts is a cobalt carbonyl in complex combination with an organic nitrogen compound.

On Sept. 30, 1980, U.S. Pat. No. 4,225,517 was issued to Gane. This patent claims a process for the production of acetaldehyde in the presence of a cobalt catalyst, an iodine or bromine promoter, one of the elements arsenic, antimony or bismuth and the additional presence of an additive which can be an inert liquid, or an acid or acid derivative, or an oxygen-containing compound, or a non-polar solvent. These selectivities reported are below 60%. In column 10, lines 5 and 6, Gane indicates that the use of a trivalent phosphorus compound resulted in the production of ethanol as the major product rather than the production of acetaldehyde.

In Japanese Publications Nos. 77/136110, and 77/136111, filed by Saito et al. and published on Nov. 14, 1977, there are disclosed cobalt catalysts promoted with an iodine compound and employing a phosphorus compound. In neither publication is there any mention of the trivalent nitrogen compounds and both show low selectivities.

Japanese Publication No. 77/133914, filed by Saito et al. and published on Nov. 9, 1977, relates to the use of cobalt, a halide promoter and at least one element of the group, arsenic, antimony and bismuth. There was no disclosure of trivalent nitrogen or trivalent phosphorus compounds and selectivities were low.

In an article by Pretzer and kobylinski, Annals New York Academy of Sciences, 333,58 (1980), the authors discussed the methanol carbonylation reaction. On page 60 they noted total inhibition of the cobalt catalyst was observed when n-butylamine was used in the catalyst charge in addition to cobalt acetoacetate and iodine. They also noted that addition of triphenylphosphine enhanced the selectivity to ethanol at the expense of all other potential products.

SUMMARY OF THE INVENTION

An improved catalyst system for the selective production of acetaldehyde and dimethyl acetal from the reaction of methanol with carbon monoxide and hydrogen (synthesis gas) has been found. This catalyst contains cobalt atoms, halogen atoms and both a trivalent nitrogen compound and a trivalent phosphorus compound utilized together within the specific ratio. The use of both trivalent nitrogen compound and trivalent phosphorus compound within the ranges defined unexpectedly results in high conversion rate or activity and high selectivity.

DESCRIPTION OF THE INVENTION

In the catalytic reactions of synthesis gas to produce organic compounds there are several criteria required of the catalyst. The catalyst must be as stable as possible, it should have a high activity or conversion rate, and it should have as high a selectivity for the desired product as possible.

Stability of the catalyst relates to how long the catalyst remains functional before either breaking down or losing its catalytic effect.

Activity or conversion rate relates to the amounts of reactants the catalyst converts to product per unit of time, generally expressed in g. mole per liter per hour (g mole/l/hr).

Selectivity relates to the quantity of desired products produced, generally expressed in mole percent, based on the total amount of products produced, both desired products and undesired products.

The goal to be achieved is high values for all three criteria and continued efforts are being made to find new catalyst compositions to reach this goal without having a significant detrimental effect on the overall process. Toward this goal the prior art has developed catalyst systems containing cobalt plus halide plus amine; cobalt plus halide plus phosphorus as well as many other systems containing variations in which diverse other components were added. Though these catalyst systems are effective for commercial practice improvement would still be desirable.

The present invention is based on the unexpected discovery that a cobalt-halide-(trivalent nitrogen plus trivalent phosphorus) catalyst is generally an unexpectedly superior catalyst to a cobalt-halide-trivalent nitrogen catalyst or a cobalt-halide-trivalent phosphorus catalyst, when used under similar conditions, for the selective production of acetaldehyde and dimethyl acetal at high conversion rates. This unexpected improvement in both selectivity and conversion rate is achieved when the catalyst components are maintained within a defined range and the amounts of trivalent nitrogen compound and trivalent phosphorus compound utilized together are within a specified ratio. Optionally a solvent and/or diluent can also be present.

The improved catalyst of this invention can be portrayed as containing the components Co-Halide-$ER_3$, wherein Co is the cobalt containing compound, Halide is the halogen containing compound and $ER_3$ is the sum of both the trivalent nitrogen compound ($NR_3$) and the trivalent phosphorus compound ($PR_3$). For further clarification $ER_3 = NR_3 + PR_3$ or $ER_3 = (NR_3$ and/or $R''CONR_2'') + (PR_3$ and/or $R_2PC_nH_{2n}PR_2)$ as hereinafter further discussed.

The fact that use of a promoting mixture of trivalent nitrogen compound in combination with the trivalent phosphorus compound with cobalt and halide forms such an excellent catalyst was completely unexpected in view of the prior art. In an article published in Annals New York Academy of Sciences, 333, 58 (1980), Wayne Pretzer and Thaddeus Kobylinski discuss the use of ligand modifiers in methanol hydroformylation and homologation reactions and on page 60 they specifically state "Total inhibition of the cobalt catalyst is observed when $(n-C_4H_9)_3N$ is used in the catalyst charge in addition to $Co(AcAc)_2$ and $I_2(N:Co=1)$." Thus, since the prior art indicates that total inhibition of the catalyst was to be expected, it was completely surprising and unexpected to find the opposite result, an improvement in both conversion rate and in selectivity with the addition of a trivalent nitrogen compounds, preferably a tertiary amine compound, to the cobalt catalyst.

It was also discovered that the cobalt-halide-$NR_3$ catalyst per se, without the presence of $PR_3$, was, surprisingly and unexpectedly, a good catalyst. Though the prior art claims such catalyst is a very poor catalyst for methanol hydroformylation, it has now been found that it is an excellent catalyst when the catalyst components are maintained within a well-defined range, even though it is not as good as the cobalt-halide-$ER_3$ catalyst.

The cobalt component of the catalyst system can be supplied from any number of sources, many of which are known to those of ordinary skill in the art. Thus, it is not necessary for an understanding thereof to specifically enumerate every suitable type and specific compound since any of the known compounds can be used. Nevertheless, descriptive of some of the useful cobalt sources are the known cobalt carboxylates such as cobalt formate, cobalt acetate, cobalt benzoate, cobalt toluate, cobalt propionate, cobalt butyrate, cobalt valerate, cobalt hexanoate, cobalt cyclohexanebutyrate, and the like; the cobalt carbonyls such as dicobalt octacarbonyl, acetyl cobalt tetracarbonyl, tricobalt dodecacarbonyl, and the like, including their phosphine substituted analogs many of which are known to those skilled in the art; the cobalt oxides such as cobalt oxide; cobalt hydroxide; cobalt carbonate; cobalt bicarbonate; cobalt. When a phosphorus substituted analog or a cobalt halide is used, proper adjustment is required to maintain the ratios as they are defined in this invention.

The cobalt concentration in the reaction can be varied from about 1 to about 40 mgm-atoms per mole of methanol charged; preferably from about 2 to about 20 mgm-atoms per mole of methanol and most preferably from about 3 to about 15 mgm-atoms per mole of methanol.

The halide component of the catalyst can be a halogen compound containing iodine, bromine or chlorine or two or more of the same, or the elemental halogen per se, or any mixtures of compounds and/or elements. The preferred is iodine or inorganic or organic compounds containing the iodine atom. The suitable halogen compounds are well known to those of average skill in this art and a complete listing is not necessary for their comprehension. Illustrative thereof one can mention iodine, hydriodic acid, cobalt iodide, potassium iodide, lithium iodide, sodium iodide, calcium iodide, ammonium iodide, methyl iodide, ethyl iodide, propyl iodide, 2-ethylhexyl iodide, n-decyl iodide, acetyl iodide, propionyl iodide; the organic ammonium iodides of the formula $R'_4NI$ and the organic phosphonium iodides of the formula $R'_4PI$ in which $R'$ is alkyl, saturated or unsaturated, substituted or unsubstituted, having from 1 to abut 10 carbon atoms or aryl, unsubstituted or substituted, having from 6 to 10 ring carbon atoms such as trimethyl ammonium iodide, tetraethyl ammonium iodide, tetra-2-ethylhexyl ammonium iodide, tetraphenyl ammonium iodide, tetramethyl phosphonium iodide, tetrapropylphosphonium iodide, tetra-2-ethylhexyl phosphonium iodide, tetrapropyl phosphonium iodide, tetra-2-ethylhexyl phosphonium iodide, tetraphenyl phosphonium iodide, methyltriphenyl phosphonium iodide, and the like; methylammonium iodide, triphenylammonium iodide, tricyclohexylammonium iodide, tri-p-tolyl-ammonium iodide, decylammonium iodide, ethylphosphonium iodide, triphenylphosphonium iodide, tricyclohexylphosphonium iodide, tri-p-tolylphosphonium iodide, and the like; also useful are bromine and its corresponding compounds and chlorine and its corresponding compounds. Any source of halogen atom can be used provided that it does not have a deleterious effect on the reaction. Again, one must maintain the defined ratios.

The amount of halogen charged is dependent upon the amount of cobalt employed. The halogen:cobalt mgm-atom ratio is at least 0.5:1 and can be as high as 20:1. It is preferably from about 1:1 to about 10:1 and most preferably from about 2:1 to about 5:1.

The phosphorus component of the catalyst is a trivalent phosphorus compound such as the simple trivalent phosphorus compounds of the formulas $PR_3$ or $P(OR)_3$ or $RP(OR)_2$ or $R_2POR$ or the polydentate trivalent phosphines of the formula $R_2PC_nH_{2n}PR_2$, or mixtures thereof, in which R is an alkyl group, saturated or unsaturated, linear or branched, having from 1 to 20 or more carbon atoms, preferably from 4 to 10 carbon atoms; or an aryl, alkaryl or aralkyl group having from 6 to 10 ring carbon atoms, preferably 6 ring carbon atoms; or cycloalkyl having from 5 to 8 ring carbon atoms, preferably 5 or 6 ring carbon atoms; and n is an integer having a value of from 2 to 8, preferably 2 to 4. The R groups may be the same or different in the molecule and they can be unsubstituted or substituted with groups which will not unduly interfere with the reaction or have a deleterious effect on it. Mixtures of the phosphorus compounds can be used if one so desires. Though those skilled in the art know the phosphorus compounds, illustrative of suitable compounds one can mention triethylphosphine, tributylphosphine, tri-2-ethylhexylphosphine, triphenylphosphine, tri(4-methoxyphenyl)phosphine, tri-p-tolylphosphine, tri(3-chlorophenyl)phosphine, diphenyl hexylphosphine, dimethyl (3-methoxyphenyl)phosphine, dibutylstearylphosphine, tribenzylphosphine, tricyclohexyphosphine, cyclohexyl dibutylphosphine, propyl diphenylphosphine, dipropyl phenylphosphine, ethyl diproxyphosphine, phenyl diethylphosphine, triethylphosphite, tributylphosphite, tridecylphosphite, trioctadecylphosphote, triphenylphosphite, tribenzylphosphite, tricyclohexylphosphite, diethylphenylphosphite, methyl diethoxyphosphine, ethyl diethoxyphosphine, butyl dibutoxyphosphine, ethyl dihenoxyphosphine, phenyl diethoxyphosphine, totyl diethoxyphosphine, diethyl ethoxyphosphine, dibutyl butoxyphosphine, cyclohexyl diethyoxyphosphine, diethyl cyclohexoxyphosphine, diethyl phenoxyphosphine, bis-(diphenylphosphino)-ethane, bis-(diethylphosphino)-propane, bis-(diphenylphosphino)-butane, bis-(diethylphosphino)-octane, and the like; many more are known in the art.

The trivalent nitrogen compound of the catalyst is an amine of the formula $NR_3$ or an amide of the formula $R''CONR_2''$ in which R is as previously defined and R" is hydrogen or alkyl, saturated or unsaturated, unsubstituted or substituted having rom 1 to about 20 carbon atoms, preferably from 4 to 10 carbon atoms, cycloalkyl, substituted or unsubstituted, having from 5 to 8 ring carbon atoms, or aryl, substituted or unsubstituted, having from 6 to 10 ring carbon atoms. Illustrative thereof are trimethylamine, triethylamine, tri-n-butylamine, tri-t-butylamine, tri-2-ethylhexylamine, methyl dibutylamine, tridodecylamine, tristearylamine, ethyl dibutylamine, tricyclohexylamine, triphenylamine, tri(4-methoxyphenyl)amine, tri(p-chloro-phenyl)amine, dibutyl phenylamine, dipentyl cyclopentylamine, ethyl diphenylamine, trinaphthylamine, tri-p-tolylamine, tribenzylamine, tri(3-methylcyclohexyl)amine, formamide, acetamide, chloracetamide, propionamide, benzamide, butylamide, N-methyl formamide, N-methylacetamide, N,N-dimethyl propionamide, N,N-dihexyl butylamide, N,N-dihexyl acetamide, 2-methyl hexylamide, N,N-isobutyl propionamide, N,N-didecyl nonamide, and the like.

As previously indicated the catalyst contains both the phosphorus component and the nitrogen component at a total concentration of $ER_3$ in which:

$$ER_3 = NR_3 + RP_3$$

Thus, $ER_3$ is the "Total $ER_3$" which is charged to the reactor; it is the sum of the millimoles of $NR_3$ plus the millimoles of $PR_3$ charged. The Total $ER_3$ charged is dependent upon the amount of halide charged with the Total $ER_3$:halide millimole ratio being from 0.1:1 to 2.8:1, preferably from 0.4:1 to 2:1 and most preferably from 0.5:1 to 1:1.

The amount or % $NR_3$ present in the Total $ER_3$ is also of significant importance. It can vary from 5% to 50%, preferably from 5% t 30% and most preferably from 10% to 25%. The % $NR_3$ is determined by the equation:

$$\% \ NR_3 = \frac{\text{mmole } NR_3}{\text{mmole } NR_3 + \text{mmole } PR_3} \times 100$$

During the reaction one can also have present an inert solvent; any of those known to be useful in this art can be used which do not have a deleterious effect on the catalytic reaction. If a solvent is utilized the solvent/methanol volume ratio can vary from 0.1:1 to about 20:1 or higher, preferably from 1:1 to about 10:1. Illustrative of preferred suitable solvents are 1,4-dioxane, ethylene glycol and the polyethylene glycols having molecular weights up to about 500 or higher if desired, as well as their mono- and di-ethers. Diphenyl ether, sulfolane, tripropylphosphine oxide, toluene, methyl acetate, butanol, propanol and similar compounds are also acceptable but in some instances they may react and/or lead to a two-phase product system which might possibly present problems in a commercial scale operation.

It has been found that when the catalytic process containing both trivalent phosphorus and trivalent nitrogen compounds is operated within the ranges defined the process provides high selectivity to acetaldehyde at commercially acceptable rates. When operated within the preferred ranges extremely high selectivity is achieved in comparison to prior processes.

It was previously indicated that a mixture of cobalt, halide and trivalent nitrogen compound (without the presence of trivalent phosphorus) is also a good catalyst, contrary to prior art allegations. In this instance, it is an effective catalyst when the catalyst components are maintained in a well defined range in which the cobalt concentration is from about 2 to 20 mgm-atoms per mole of methanol, preferably from 3 to 15 mgm-atoms per mole; the halogen:cobalt mgm-atom ratio is greater than 1:1, preferably from 2:1 to 5:1; and the $NR_3$:halogen ratio is between 0.1:1 to 3:1, preferably from 0.5:1 to 2:1. While this is an effective catalyst, it does not have the high selectivity and conversion rates that are observed when a mixture of $NR_3$ and $PR_3$ components is used under the conditions set forth above.

The reaction is carried out at a temperature of from about 100° C. to 250° C., preferably from 120° C. to 200° C. and most preferably from 140° C. to 180° C.

The pressure of the reaction can be from about 750 psig to 8,000 psig and most preferably from 3,000 psig to 6,000 psig.

The ratio of $CO:H_2$ in the synthesis gas feed mixture can range from 0.1:1 to 10:1, preferably from 0.25:1 to 4:1 and most preferably from 0.33:1 to 2:1.

The reaction time varies depending upon the reaction parameters, reactor size and charge, and the individual components employed at the specific process conditions.

The experiments and examples detailed below were carried out in a Hasteloy ® steel autoclave reactor having a volume of 300 ml, which was equipped with temperature and pressure sensing means, heating and cooling means, agitator and inlet and outlet means for introducing and removing components from the reactor. The autoclaves used in the synthesis gas reactions are well known in the art.

Prior to charging the reactants (methanol, catalyst, diluent), the autoclave was washed with methanol at 100° C. under a synthesis gas pressure of 500 to 1,000 psig by agitating for 30 minutes. The autoclave was drained, rinsed with dry acetone, and dried with nitrogen. The liquid components were charged to the cleaned autoclave first and then the solid components were added and stirred. The autoclave was closed, purged with synthesis gas and then pressurized to 3,000 psig with synthesis gas. The autoclave contents were heated to the selected temperature, with agitation (usually 750 rpm), in about 45 minutes. As soon as the desired temperature was reached, the autoclave was brought to the desired pressure plus 250 psig. The reaction was allowed to consume synthesis gas until the pressure had fallen to 250 psig below the desired pressure. The reactor was then repressurized to 250 psig above the desired pressure. One such cycle is considered 500 psig gas uptake. Unless otherwise specified the reactions were allowed to proceed until 3,000 psig synthesis gas uptake had occurred.

At the end of a reactor run, the contents were cooled, generally to about 10° C. A vapor phase sample was taken for gas liquid chromatograph analysis; the gas phase was vented through two dry-ice acetone traps and then through a 10 liter saturated solution of calcium hypochlorite to remove metal carbonyls. The reactor was pressurized three times with nitrogen, 90 psig, and vented through the same system.

The residual reactor contents were dumped into a chilled pressure bottle and sealed. Subsequent analysis was performed using a Hewlett-Packard Model 5880 gas chromatograph equipped with two columns one-eighth inch in diameter by ten feet long connected in series. The columns were packed with Chromosorb 101.

The following examples serve to further illustrate this invention. In all examples conversion rates and selectivities include acetaldehyde plus the acetaldehyde equivalents in the dimethylacetal.

EXAMPLE 1

(A) A series of reactions was conducted by the procedure described above using 37.5 ml of methanol, 112.5 ml of the diethyl ether of ethylene glycol as the inert solvent, cobalt (II) acetate tetrahydrate (4 mmole cobalt), elemental iodine (7 mmole) and varying amounts of triphenylamine as the trivalent nitrogen compound $NR_3$. In this series there was no trivalent phosphorus present. The temperature was maintained at 170° C. and the pressure at 5,000 psig±250 psig during the reaction period required for the uptake of 3,000 psig of synthesis gas, which gas had a $CO:H_2$ mole ratio of 1:1.5. The I:Co ratio was 3.5:1. The amount of triphenylamine was varied to observe the effect variation of the $NR_3$:I ratio would have on the conversion rate and the selectivity to acetaldehyde. The results are tabulated below:

TABLE I-A

| $NR_3$:I (mmole) | Conversion Rate (g mole/l/hr) | Selectivity (mole %) |
|---|---|---|
| 0.55 | 2.0 | 68 |
| 1.1 | 2.1 | 79 |
| 1.5 | 1.8 | 78 |

That such significant conversion rates and selectivity were achieved was completely unexpected and unobvious in view of the statements by W. Pretzer and T. Kobylinski in their article referred to above.

(B) For comparison purposes a second series was carried out under the same reaction conditions desribed in Section (A). However, in this series there was no trivalent nitrogen compound present; instead the trivalent phosphorus compound triphenylphosphine, $PR_3$, was used at the same $PR_3$:I ratios. The results are tabulated below:

TABLE I-B

| $PR_3$:I (mmole) | Conversion Rate (g mole/l/hr) | Selectivity (mole %) |
|---|---|---|
| 0.55 | 2.0 | 79 |
| 1.1 | 3.5 | 89 |
| 1.5 | 2.6 | 86 |

As expected, the conversion rates and selectivities in Section (B) were higher than in Section (A); however, in light of the article by W. Pretzer and T. Kobylinski it was surprising and unexpected to find that the reaction in Section (A) did proceed as well as it did when the sole additive was triphenylamine.

In the subsequent example it was unexpectedly and surprisingly found that the use of a mixture of trivalent nitrogen compound, $NR_3$, plus trivalent phosphorus compound, $PR_3$, resulted in both conversion rates and selectivities to acetaldehyde that were considerably higher than those observed in Sections (A) or (B) of Example 1.

EXAMPLE 2

A series of reactions was carried out under the same reaction conditions described in Section (A) of Example 1. However, in this series a mixture of trivalent nitrogen compound ($NR_3$=triphenylamine) and trivalent phosphorus compound ($PR_3$=triphenylphosphine) at a Total $ER_3$:I ratio of 1.1:1 was used. The percent of trivalent nitrogen compound, $\%NR_3$, was varied and for comparison the results achieved in Example 1, Sections (A) and (B), are included as Runs (a) and (g) in Table II, together with the results of this series.

TABLE II

| Run | $NR_3$ (mmole) | $PR_3$ (mmole) | $\%NR_3$ | Conversion Rate (g mole/l/hr) | Selectivity (mole %) |
|---|---|---|---|---|---|
| a | 0 | 15.4 | 0 | 3.5 | 89 |
| b | 0.77 | 14.63 | 5 | 4.2 | 89 |
| c | 1.54 | 13.86 | 10 | 6.7 | 87 |
| d | 2.31 | 13.09 | 15 | 4.6 | 89 |
| e | 3.86 | 11.55 | 25 | 4.1 | 88 |
| f | 7.7 | 7.7 | 50 | 2.7 | 83 |
| g | 15.4 | 0 | 100 | 2.1 | 79 |

The data shows, when consideration is given to the prior art disclosure of W. Pretzer and T. Kobylinski, a completely unexpected increase in conversion rate coupled with high selectivity when mixtures of $NR_3$ and $PR_3$ compounds are used. At $\%NR_3$ concentrations of from 5% to 50% and Total $ER_3$:ratio of 1.1:1. The conversion rate was much higher in Runs b to e as compared to Runs (a) and (g) and maximized, under the conditions of this example, at a $\%NR_3$ of 10% in Run c. Though Run (f) starts to show a decline in conversion rate at a $\%NR_3$ concentration of 50%, this was still an unexpectedly high conversion rate in view of the Pretzer and Kobylinski prior art teachings.

EXAMPLE 3

A series of reactions was carried out in a manner similar to that described in Example 2, In this series the Total $ER_3$:I ratio was 0.55:1 with the percent of trivalent nitrogen compound varying from zero to 100 percent.

TABLE III

| Run | $NR_3$ (mmole) | $PR_3$ (mmole) | $\%NR_3$ | Conversion Rate (g mole/l/hr) | Selectivity (mole %) |
|---|---|---|---|---|---|
| a | 0 | 7.7 | 0 | 2 | 79 |
| b | 0.77 | 6.93 | 10 | 1.4 | 80 |
| c | 1.54 | 6.16 | 20 | 2.1 | 76 |
| d | 2.31 | 5.39 | 30 | 2.4 | 86 |
| e | 7.7 | 0 | 100 | 2 | 68 |

Though the enhancement in selectivity and conversion rate is not as marked as in Example 2, the trend at the Total $ER_3$:I ratio of 0.55:1 was still apparent. At this ratio best selectivity and rate were observed at a 30% $NR_3$ concentration, Run (d). Though Runs (b) and (c) show lower values than Run (d), the overall general results in combined rate and selectivity are an improvement over either Run (a) or Run (b).

EXAMPLE 4

A series of reactions was carried out in a manner similar to that described in Example 2. In this series 12 mmole of cobalt, 18 mmole of elemental iodine, 75 ml of methanol and 75 ml of the diethyl ether of ethylene of glycol were used in each reaction and the pressure was maintained at 3,000 psig±250 psig. The Total $ER_3:I$ ratio was maintained at 1.1:1. This series differed from Example 2 in that it was operated at a lower pressure, at a higher cobalt atom concentration and with less solvent. Significant enhancement in both rate and selectivity was observed in Runs (b) and (c) at 10% and 20% $NR_3$ concentrations. At 30% $NR_3$ concentration significant enhancement was observed in selectivity but not in rate. The results are tabulated below:

TABLE IV

| Run | $NR_3$ (mmole) | $PR_3$ (mmole) | % $NR_3$ | Conversion Rate (g mole/l/hr) | Selectivity (mole %) |
|---|---|---|---|---|---|
| a | 0 | 39.6 | 0 | 7.8 | 87 |
| b | 3.96 | 35.64 | 10 | 8.3 | 89 |
| c | 7.92 | 31.68 | 20 | 8.6 | 90 |
| d | 11.88 | 27.72 | 30 | 6.5 | 92 |

EXAMPLE 5

A series of experiments was carried out as described in Section (A) of Example 1 with the exception that the triphenylamine was replaced by dimethylformamide in the amounts shown in Table V. The concentrations of the other components and the reaction conditions were as described in Example 1, Section (A). It was observed that higher rates and selectivities were achieved with the formamide in comparison to the rates and selectivities achieved with the triphenylamine.

TABLE V

| Amide:I (mmole) | Conversion Rate (g mole/l/hr) | Selectivity (mole %) |
|---|---|---|
| 0.55 | 2.1 | 87 |
| 1.1 | 2.5 | 89 |
| 1.5 | 3.2 | 89 |

I claim:

1. In a catalytic reaction process for selectively producing acetaldehyde and dimethylacetal by the reaction of methanol, hydrogen and carbon monoxide at a pressure of from 750 psig to 10,000 psig, a temperature of from 100° C. to 250° C. and a $CO:H_2$ mole ratio of 0.1:1 to 10:1 and wherein the catalyst consists essentially of cobalt and halide atoms, the improvement consisting of carrying out the reaction in contact with a promoting mixture consisting essentially of (i) a trivalent nitrogen compound of the general formula $NR_3$ or $R''CONR_2''$ and (ii) a trivalent phosphorus compound of the general formula $PR_3$ or $R_2PC_nH_{2n}PR_2$, wherein R is an alkyl group having 1 to 20 carbon atoms, or an aryl group having 6 to 10 ring carbon atoms, or a cycloalkyl group having 5 to 8 ring carbon atoms; R" is hydrogen, or an alkyl group having 1 to 20 carbon atoms, or an aryl group having 6 to 10 ring carbon atoms, or a cycloalkyl group having 5 to 8 ring carbon atoms and n is an integer having a value of from 2 to 8; wherein Total $ER_3$ is the sum of trivalent nitrogen compound and trivalent phosphorus compound and Total $ER_3$:halide mmole ratio is from 0.1 to 2.8:1 and wherein the amount of trivalent nitrogen compound in Total $ER_3$ is from 5 mole % to 50 mole %.

2. The improved process as claimed in claim 1, wherein R is an alkyl group having 4 to 10 carbon atoms.

3. The improved process as claimed in claim 1, wherein R" is an alkyl group having 4 to 10 carbon atoms.

4. The improved process as claimed in claim 1, wherein n has a value of 2 to 4.

5. The improved process as claimed in claim 2, wherein n has a value of 2 to 4.

6. The improved process as claimed in claim 3, wherein n has a value of 2 to 4.

7. The improved process as claimed in claim 1, wherein Total $ER_3$:halide mmole ratio is from 0.4:1 to 2:1.

8. The improved process as claimed in claim 4, wherein Total $ER_3$:halide mmole ratio is from 0.4:1 to 2:1.

9. The improved process as claimed in claim 5, wherein Total $ER_3$:halide mmole ratio is from 0.4:1 to 2:1.

10. The improved process as claimed in claim 6, wherein Total $ER_3$:halide mmole ratio is from 0.4: to 2:1.

11. The improved process as claimed in claim 1, wherein Total $ER_3$:halide mmole ratio is from 0.5:1 to 1:1.

12. The improved process as claimed in claim 1, wherein the amount of trivalent nitrogen compound in Total $ER_3$ is from 5 mole % to 30 mole %.

13. The improved process as claimed in claim 8, wherein the amount of trivalent nitrogen compound in Total $ER_3$ is from 5 mole % to 30 mole %.

14. The improved process as claimed in claim 9, wherein the amount of trivalent nitrogen compound in Total $ER_3$ is from 5 mole % to 30 mole %.

15. The improved process as claimed in claim 10, wherein the amount of trivalent nitrogen compound in Total $ER_3$ is from 5 mole % to 30 mole %.

16. The improved process as claimed in claim 1, wherein the amount of trivalent nitrogen compound in Total $ER_3$ is from 10 mole % to 25 mole %.

17. The improved process as claimed in claim 8, wherein the amount of trivalent nitrogen compound in Total $ER_3$ is from 10 mole % to 25 mole %.

18. The improved process as claimed in claim 9, wherein the amount of trivalent nitrogen compound in total $ER_3$ is from 10 mole % to 25 mole %.

19. The improved process as claimed in claim 10, wherein the amount of trivalent nitrogen compound in Total $ER_3$ is from 10 mole % to 25 mole %.

20. The improved process as claimed in claim 1, wherein the promoting mixture consisted essentially of the trivalent nitrogen compound only.

21. The improved process as claimed in claim 1, wherein the halide is iodine.

22. The improved process as claimed in claim 4, wherein the halide is iodine.

23. The improved process as claimed in claim 7, wherein the halide is iodine.

24. The improved process as claimed in claim 11, wherein the halide is iodine.

25. The improved process as claimed in claim 12, wherein the halide is iodine.

26. The improved process as claimed in claim 16, wherein the halide is iodine.

27. The improved process as claimed in claim 20, wherein the halide is iodine.

28. The improved process as claimed in claim 1, wherein the promoting mixture contains triphenylamine and triphenylphosphine.

29. The improved process as claimed in claim 1, wherein the trivalent nitrogen compound is dimethylformamide.

* * * * *